United States Patent [19]

Guerrant et al.

[11] Patent Number: 5,124,252

[45] Date of Patent: Jun. 23, 1992

[54] IN VITRO TEST FOR FECAL LEUKOCYTES

[75] Inventors: Richard L. Guerrant, Charlottesville, Va.; Amelia G. Lee, Silver Spring, Md.; William H. Cooper, Charlottesville, Va.

[73] Assignee: University of Virginia Alumni Patents Foundation, Charlottesville, Va.

[21] Appl. No.: 442,309

[22] Filed: Nov. 28, 1989

[51] Int. Cl.[5] ................ G01N 33/559; G01N 33/551; G01N 33/546

[52] U.S. Cl. ................ 435/7.24; 435/7.92; 435/7.94; 436/514; 436/534

[58] Field of Search ............ 435/7.92, 7.24, 7.94; 436/514, 533, 534

[56] References Cited

U.S. PATENT DOCUMENTS

| 4,184,849 | 1/1980 | Cambiaso et al. | 436/533 |
| 4,358,535 | 11/1982 | Falkow et al. | 435/38 |
| 4,689,295 | 8/1987 | Taber et al. | 435/34 |

OTHER PUBLICATIONS

Leffell et al., "Association of Lactoferrin with Lysozyme in Granules of Human Polymorphonuclear Leukocytes", Infection and Immunity, 6:760-765 (USA 1972).

Korzeniowski et al., "Value of Examination for Fecal Leukocytes in the Early Diagnosis of Shigellosis", Am J Trop Med Hyg, 28:1031-1035 (USA 1979).

Guerrant et al., "Evaluation and Diagnosis of Acute Infectious Diarrhea", The American Journal of Medicine, 78:90-98 (USA 1985).

Oneson et al., "Leukocyte Esterase Activity and Nitrite Test as a Rapid Screen for Significant Bacteriuria", American Journal of Clinical Pathology, 83:84-87 (USA 1985).

Hetherington et al., "An Enzyme-Linked Immunoassay (ELISA) for Measurement of Lactoferrin", Journal of Immunological Methods, 65:183-190 (USA 1983).

*Primary Examiner*—Mary E. Ceperley
*Attorney, Agent, or Firm*—James Creighton Wray

[57] ABSTRACT

An in vitro test for determining the presence of leukocytes in a fecal sample which is sensitive to the numbers of fecal leukocytes typically found in inflammatory diarrheal specimens, by testing the fecal sample with an assay utilizing an antibody for lactoferrin.

4 Claims, 1 Drawing Sheet

IN VITRO TEST FOR FECAL LEUKOCYTES

BACKGROUND OF THE INVENTION

1. Field of the Invention

The present invention relates to diagnosis of inflammatory diarrhea, using a simple, convenient assay that requires minimal laboratory skills or experience.

2. Prior Art

A need exists for a simple, reliable in vitro test for fecal leukocytes (even after they are morphologically disrupted), to indicate that a subset of patients with the common problem of diarrhea that is inflammatory and thus requires specific, more costly diagnostic and therapeutic attention.

Diarrheal illnesses are extremely common (causing 2 to 12 or more illnesses per person per year) throughout the world, and often pose diagnostic and therapeutic questions for the physician. Fortunately, important diagnostic clues can be obtained by considering whether the diarrhea is a noninflammatory process arising typically from the upper small bowel, or whether it is an inflammatory diarrhea arising from an invasive process in the ileum or colon. Although the majority of cases are noninflammatory and will often respond to simple oral rehydration therapy, it is important to distinguish the invasive, inflammatory diarrheas, which are usually caused by Shioella, Salmonella, Campylobacter or Clostridium bacteria that may be more severe and should be the focus of more expensive culturing for these invasive pathogens. The invasive, inflammatory diarrheas may also require specific antibiotic treatment. A particularly helpful diagnostic clue to distinguishing inflammatory from noninflammatory diarrheas has been the examination for large numbers of leukocytes (white blood cells or "pus cells") in the diarrheal fecal specimens themselves. However, this requires that the physician or a skilled technician promptly examine mucus from a cup fecal specimen under a microscope, stained for clearly distinguishable leukocytes in the fecal debris. This requires the immediate availability of a skilled person with a microscope to stain and examine fresh fecal specimens in the clinic or emergency area where the patient is seen. Despite extensive efforts, this is difficult to accomplish, especially with this extremely common problem in a busy clinic setting.

There are many potential markers for leukocytes in the primary and secondary granules. Leukocyte esterase was explored as a potential marker for fecal leukocytes, since an analogous test exists for leukocytes in urine. However, it was discovered that leukocyte esterase was non-specifically positive for all stool samples, both those with and without leukocytes.

SUMMARY OF THE INVENTION

A simple, in vitro test for a leukocyte marker was developed that is sensitive to the numbers of fecal leukocytes typically found in inflammatory diarrheal specimens and that can be quickly and easily done with a minimum of training, either in the clinic or later (after transportation or storage) in the laboratory. The marker found most specific for leukocytes in fecal specimens is based on lactoferrin, an iron-binding glycoprotein found concentrated in secondary granules in leukocytes (Hetherington et. al. "An Enzyme-Linked Immunoassay (ELISA) for Measurement of Lactoferrin", J IMMUN METH, 65:183–190 (U.S.A.) 1983). Standard immunoassay methods of radial immunodiffusion, latex agglutination and enzyme-linked immunosorbent assays (ELISA) that employ antibodies against lactoferrin have proved successful in detecting specimens. However, the latex agglutination method seems the simplest and most applicable in vitro test.

These and further and other objects and features of the invention are apparent in the disclosure, which includes the above and ongoing written specification, including the claims and the drawings.

DETAILED DESCRIPTION OF THE INVENTION

Figure 1:
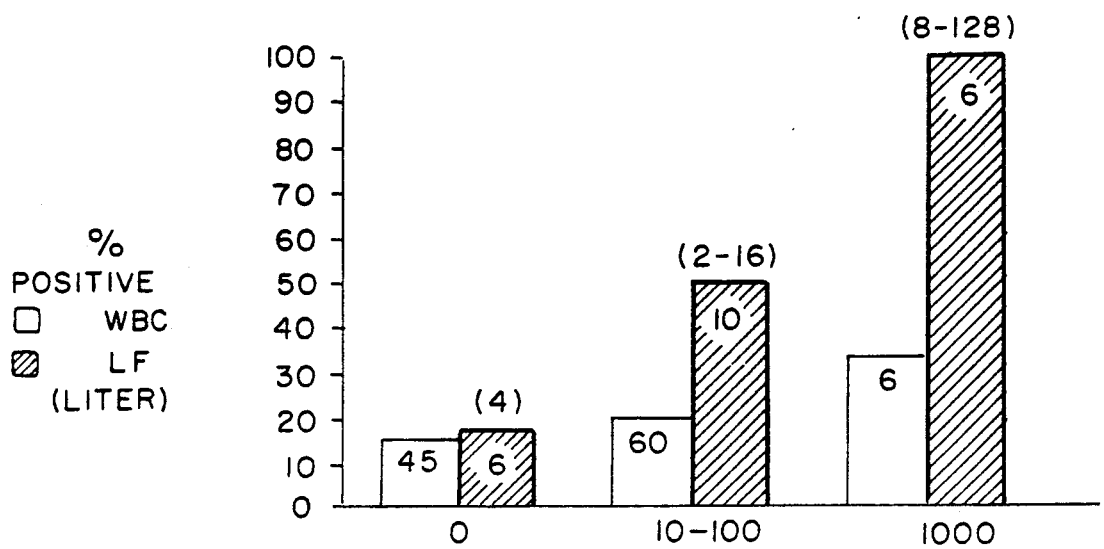
FIG. 1 graphically illustrates results of 22 fecal specimens tested for *C. difficile* cytotoxin tested with the leukocyte lactoferrin latex agglutination assay showing that with increasing cytotoxin titer, an increasing percent (to 100%) of lactoferrin, evidence of an inflammatory process.

This in vitro test for a leukocyte marker must be sensitive to the numbers of fecal leukocytes typically found in inflammatory diarrheal specimens. Typically, at least 5,000 to 10,000 polymorphonuclear neutrophils per $mm^3$ are found in inflammatory diarrheal specimens.

(a) Radial Immunodiffusion Assay

Studies were conducted using the commercially available LC-Partigen radial immunodiffusion plates (Calbiochem) for lactoferrin. The leukocytes were obtained from fresh, whole blood processed with a neutrophil isolation kit. The fecal suspensions with and without leukocytes were initially mixed with an equal amount of 0.1% Triton-X to lyse the leukocytes (an addition that was subsequently found to be unnecessary). Forty microliters of this suspension was placed in the wells and the plates were checked daily for visible rings around the wells. Within three days, measurable rings were visible around the wells which had stool samples with fecal leukocytes added and were absent in samples without fecal leukocytes. The ring size with fecal leukocytes at 10,000/$mm^3$ was 9.05 mm. The ring size with fecal samples that included 7,700 leukocytes/$mm^3$ was 7.05 mm and no ring was seen in fecal samples with no leukocytes. Similar results were obtained after 10 days' refrigeration of the fecal-leukocyte suspension as well.

Because the Calbiochem LC-Partigen kits became unavailable, continuing work necessitated preparation of plates with purchased anti-lactoferrin antibody. The preparation of plates for radial immunodiffusion assay was made by adding 6 ml of 1% agarose containing 1:100 rabbit anti-lactoferrin antibody (30 ul per 6 ml agarose per 2×3 The rabbit anti-human lactoferrin was obtained from Sigma Company, St. Louis, MI (Catalog #L-3262). The agarose was prepared using 1% low gel temperature agarose (Sea Plaque from FM Corporation), 3% polyethylene glycol-6000 from Fisher Scientific and 100 ml phosphate buffered saline. When the agar covered slides were ready for use, 2 mm wells were punched that each readily hold 5 microliters of antigen preparation each.

Using these methods for radial immunodiffusion, dose response curves with purified lactoferrin (Sigma Chemical Company, St. Louis, MI) showed it was detectable at 0.02–0.03 mg/ml (ug/mm$^3$) with a ring size of 4.1–4.3 mm respectively. Repeated studies with human PMN's (polymorphonuclear neutrophils) revealed optimal sensitivity of approximately $2.08 \times 10^3$ PMN/mm$^3$, giving a zone diameter of 4.7 mm. This corresponds to a calculated lactoferrin concentration of 0.0104 ug/ul based on the approximate concentration of 1 ng lactoferrin per 200 PMN's (Hetherington et al. "An Enzyme-Linked Immunoassay (ELISA) for Measurement of Lactoferrin", J IMMUN METH, 65:183-190 (U.S.A.) 1983). This result using 0.3% cetyl trimethyl ammonium bromide (CTAB, a detergent used to lyse neutrophils for their release of lactoferrin) was slightly better than that seen in the absence of CTAB, and was in the same general range of radial immunodiffusion assay results with purified lactoferrin noted above. Thus the sensitivity of radial immunodiffusion appeared to be approximately 2000 PMN's/mm$^3$, a number far lower than the expected concentration of leukocytes (PMN's) in inflammatory fecal specimens, judging by microscopy with numerous leukocytes per high power field. Natural inflammatory diarrheal specimens revealed two patients with documented Salmonella gastroenteritis showing distinct rings ranging from 4 to 13 mm in size, as well as two patients with *C. difficile* cytotoxin giving rings of 7.0 to 8.4 mm. In addition, the normal stool specimen was repeatedly negative on three different occasions. CTAB and Triton detergents did not seem to add any sensitivity to naturally inflammatory fecal specimens.

(b) Latex Agglutination Assay

For studies using latex agglutination, Bacto-latex 0.81 beads (Code 3102, Difco Laboratories, Detroit, MI) were coated with rabbit anti-human lactoferrin (Sigma Chemical Company Product #L-3262, St. Louis, MS) as follows: 2.5 ml of beads were centrifuged at 3000 rpm for 30 minutes, washed with 5 ml glycine buffer (7.3 g glycine, 10 g NaCl, in 1 liter distilled water adjusted to pH 8.2–8.3) and then resuspended in 5 ml of glycine buffer to provide an approximate 1% suspension of beads. To this latex bead suspension was added 0.35 ml rabbit antilactoferrin antibody and the mixture was incubated at 37° C. for 1 hour, after which the antibody-coated beads were spun and resuspended in 5 ml buffer to which 0.005 g azide (0.1%) and 0.05 g bovine serum albumin (1%) were added and the coated bead suspension was stored at 4.C until used. Studies with titrations or purified lactoferrin revealed readily apparent agglutination of these latex beads with 0.004–0.0016 mg/ml lactoferrin, at least one log more sensitive than the radial immunodiffusion (RID) assay mentioned above. This level of greater sensitivity of latex agglutination was also seen with ficol-hypaque separated human PMN's as well with a 1:100 dilution being positive when RID detected only a 1:8 dilution. In addition, leukocytes added to stools as well as the *Salmonella* and 4 *C. difficile* cases were positive in the latex agglutination assay. Furthermore, three additional control specimens tested on 7 different occasions were all negative. Importantly, these immunoassay results remained clearly positive even after *C. difficile* cytotoxin totally destroyed the PMN morphology over 24 hours in refrigerated specimens.

Figure 2:
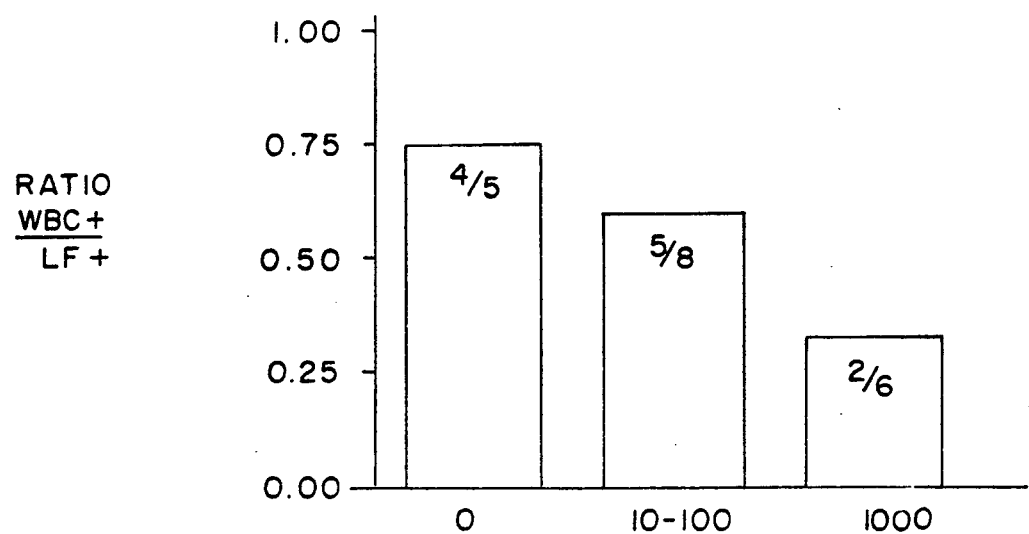
FIG. 2 graphically illustrates the increasing titer of cytotoxin which is associated with increasing titers of lactoferrin, but decreasing appearance of leukocytes, which demonstrates the destruction of leukocytes by the cytotoxin analogous to that seen in vitro.

22 fecal specimens were tested with the leukocyte lactoferrin latex agglutination assay for *C. difficile* cytotoxin with the results shown in FIG. 1. These results show that with increasing cytotoxin titers, an increasing percent (to 100%) have lactoferrin evidence of an inflammatory process. Remarkably, as shown in FIG. 2, the increasing titer of cytotoxin is associated with increasing titers of lactoferrin but decreasing appearance of leukocytes by microscopy, demonstrating the destruction of leukocytes by the cytotoxin analogous to that seen in vitro.

Further data from children with diarrhea in the northeast of Brazil have shown that specimens from 16 of 17 children with 114 5 or more fecal leukocytes per high power field on microscopy with methylene blue stain had lactoferrin latex agglutination titers of $\geq 1:50$. In contrast, only 3 of 12 methylene blue stained specimens with less than 1 leukocyte per high power field had lactoferrin titers of $\geq 1:50$. Furthermore, despite occasional positives at lower titers, none of 7 specimens from normal control children had lactoferrin titers of $\geq 1:50$.

(c) Enzyme-Linked Immunosorbent Assay (ELISA)

Studies with the development of an ELISA for lactoferrin suggest that it may be even more sensitive than the RID or latex agglutination assays. However, as noted above, the need for increased sensitivity may be unnecessary or even inappropriate. For the ELISA testing, wells were coated with varying concentrations of lactoferrin in a sodium bicarbonate buffer at room temperature for 2–3 hours or overnight at 4° C. Wells and microtiter plates were then washed 3 times with PBS-tween and 1% BSA was added to fill the wells for 30–60 minutes to block nonspecific sites, followed by washing 3 times with PBS-tween. Thereafter 50 ul of rabbit anti-human lactoferrin antibody (at 1:250 dilution, probably optimal with 1:100 and 1:500 also being effective) was added to each well, followed by 40 minutes incubation at 37° C. (or 2 hours at room temperature), followed by washing 4 times with PBS-tween. Then 50 ul of goat anti-rabbit IgG (Rockland Laboratories, Gilbertsville, PA) with peroxidase conjugation (at 1:1000 dilution) was added for 40 minutes at 37° C. (or 2 hours at room temperature), followed by washing 5 times in PBS-tween. Thereafter, 200 ul of activated peroxidase substrate was added, followed by 45 minutes incubation at room temperature in the dark, after which this was read both visually and spectrophotometrically. The apparent sensitivity was 0.001 ug/ul or less lactoferrin, with conjugate dilution of 1000 and primary rabbit antibody dilutions of 1:250, probably representing the optimal conditions for assay. The ELISA technology could also be employed in detection of leukocytes, possibly using a dipstick technology.

While the invention has been described with reference to specific embodiments, modifications and variations of the invention may be constructed without departing from the scope of the invention, which is described in the following claims.

I claim:

1. A method for distinguishing inflammatory diarrhea from noninflammatory diarrhea, comprising the steps of:

providing a fecal sample suspected of containing leukocytes;

testing the fecal sample with an assay utilizing an antibody to lactoferrin that is sensitive to the numbers of fecal leukocytes typically found in inflammatory diarrhea samples; and observing the fecal sample for the presence of lactoferrin.

2. The method of claim 1, wherein a radial immunodiffusion assay is utilized.

3. The method of claim 1, wherein a latex agglutnation assay is utilized.

4. The method of claim 1, wherein a enzyme-linked immunosorbent assay is utilized.

* * * * *